United States Patent [19]

Shimizu et al.

[11] 4,000,088
[45] Dec. 28, 1976

[54] OXIDATION CATALYST FOR THE MANUFACTURE OF METHACRYLIC ACID

[75] Inventors: Hitoshi Shimizu; Kazuo Ishimi, both of Takasaki, Japan

[73] Assignee: Nippon Kayaku Co., Ltd., Tokyo, Japan

[22] Filed: June 3, 1974

[21] Appl. No.: 476,073

[52] U.S. Cl. .............................. 252/437; 252/435; 260/530 N
[51] Int. Cl.² ........................................ B01J 27/18
[58] Field of Search ........................... 252/437, 435

[56] References Cited

UNITED STATES PATENTS

| | | | |
|---|---|---|---|
| 2,881,212 | 4/1959 | Idol et al. | 252/437 X |
| 2,904,580 | 9/1959 | Idol | 252/437 X |
| 3,265,635 | 8/1966 | Barker | 252/437 |
| 3,342,849 | 9/1967 | Brill et al. | 252/437 X |
| 3,668,147 | 6/1972 | Yoshino et al. | 252/437 X |
| 3,761,516 | 9/1973 | Khodgiar | 252/437 X |

*Primary Examiner*—Patrick P. Garvin
*Attorney, Agent, or Firm*—Russell & Nields

[57] ABSTRACT

This invention relates to a catalyst for the oxidation of methacrolein to produce methacrylic acid. The catalyst has the following composition:

$Mo_a P_b Sb_c Cu_d Cr_e O_f (NH_4)_g$ where $a$ is fixed at 12, $b$ assumes a value of 1 to 4, $c$ a value of 0.1 to 7, $d$ a value of 0.1 to 5, $e$ a value of 0 to 6, $g$ a value of 0 to 3.5 and $f$ a value, usually 35 to 80, which is automatically determined by the valence of the other atoms.

3 Claims, No Drawings

OXIDATION CATALYST FOR THE MANUFACTURE OF METHACRYLIC ACID

DETAILED DESCRIPTION OF THE INVENTION

This invention relates to a process for the manufacture of methacrylic acid by the oxidation of methacrolein and the oxidation catalyst.

More specifically, this invention relates to a process for the manufacture of methacrylic acid characterized by using a catalyst, shown herein below, in the production of methacrylic acid by the oxidation of methacrolein with molecular oxygen or a molecular oxygen-containing gas, and the oxidation catalyst having the composition as follows;

$$Mo_a P_b Sb_c Cu_d Cr_e O_f (NH_4)_g$$

(wherein, the subscripts; $a$, $b$, $c$, $d$, $e$ and $f$ denote the numbers of molybdenum, phosphorus, antimony, copper, chromium and oxygen atoms respectively and the subscript $g$ denotes the number of ammonium groups and, where $a$ is fixed at 12, $b$ assumes a value of 1 to 4, $c$ a value of 0.1 to 7, $d$ a value of 0.1 to 5, $e$ a value of 0 to 6 and $g$ a value of 0 to 3.5 respectively and $f$ a value, usually 35 to 80, which is automatically determined by the valence of the other atoms).

Heretofore, many catalysts have been proposed for use in the synthesis of unsaturated carboxylic acids by the gaseous phase oxidation of unsaturated aldehydes such as acrolein and methacrolein.

For example, U.S. Pat. No. 2,881,212 suggests a catalyst of the phosphorus-molybdenum system. With this catalyst, however, the methacrylic acid-producing activity is low and the methacrylic acid yield is only 6.6%.

Japanese Pat. No. 23367/1971 suggests a catalyst of the phosphorus-molybdenum-chromium system. With this catalyst, the methacrolein conversion is 95.1%, the methacrylic acid selectivity is 60.1% and the methacrylic acid yield is 57.2% under the severe condition of a 380° C reaction temperature. Evaluation of these known catalysts, from the commercial point of view, leads to the conclusion that it is desirable to develop an oxidation catalyst which can provide higher activity and selectivity at lower reaction temperatures.

With a view to overcoming the deficiencies of conventional catalysts, the inventors, during their research sought a catalyst which could provide a high methacrolein conversion at low reaction temperatures and could produce methacrylic acid at a high selectivity and yet enjoy a long serviceable life. They have consequently accomplished the present invention.

The aforementioned catalyst, according to the present invention, manifests a new catalytic activity in the oxidation reaction of methacrolein: This catalyst is highly active at low temperatures, suggesting a profound commercial significance, permits methacrylic acid to be produced at a high selectivity and provides catalytic acitivity for a long duration.

When the catalyst of the invention is used, the conversion of methacrolein is high at low reaction temperatures and, even at such a high conversion, there is very little occurrence of carbon dioxide and carbon monoxide, which are the complete oxidation products of methacrolein. Consequently, the amount of heat evolved in the course of reaction is small, the temperature is uniform throughout the catalyst bed and the formation of acetic acid, acrylic and acetone as by-products in the reaction of methacrylic acid formation is repressed, so that the subsequent refining operation can be rendered with extreme simplicity. The fact that the reaction temperature is low and the amount of heat evolved during the reaction is small means that the control of the reaction is easy and consequently the commercial merit of this invention is enormous.

In the present invention, a catalyst is found desirable when it is composed of the aforementioned components at the proportions shown below:

$$a : b : c : d : e : f : g = 12 : 1.5-3.5 : 0.5 - 6 : 0.3 - 4.5 : 0.1 - 4 : 40 - 70 : 1 - 3.5$$

The catalyst proves more desirable when the proportions of the components fall within the following range.

$$a : b : c : d : e : f : g = 12 : 2 - 3 : 2 - 4 : 0.5 - 2.5 : 0.5 - 1.5 : 45 - 57 : 2 - 3$$

Though the chemical structure of the catalyst to be used for this invention is not definitely known, it is believed to be made up of oxides of individual components plus complicated hetero-poly acids.

The reactants which are involved in the process of this invention are methacrolein and molecular oxygen or a molecular oxygen-containing gas. Generally, air is used as the molecular oxygen-containing gas.

The raw feed gas may contain inert gases such as nitrogen, carbon dioxide, etc.

The desirable molar ratio of methacrolein and oxygen which are contained in the raw feed gas is 1 : 0.5 - 15, preferably 1 : 1 - 7.

It is desirable that the raw feed gas be mixed with water. Generally, therefore, the feed gas is mixed with steam so that steam is present therein at a molar ratio of 1 - 20 based on methacrolein.

As to the preparation of the catalyst of this invention, a generally known method can be applied. For example, a catalyst is prepared by mixing starting materials containing the component elements, where necessary, in conjunction with aqueous ammonia water, drying the resulting mixture and calcining the dried mass between 300°- 500° C, or preferably between 350°- 430° C.

In the preparation of the catalyst for use in this invention, various starting substances can be used as sources for the component elements. They may be in the form of oxides, metals, metal salts, acids or bases containing the components elements.

Possible starting materials for molybdenum include molybdic acid, ammonium molybdate, molybdenum oxide and phosphomolybdic acid; those for phosphorus include orthophosphoric acid, pyrophosphoric acid, ammonium phosphate and phosphomolybdic acid; those for antimony include antimony trioxide, antimony pentoxide and antimony trichloride; those for copper include copper molybdate, copper chromate, copper phosphate, copper pyrophosphate and copper hydroxide; and those for chromium include ammonium chromate, chromic acid, chromium oxide, copper chromate and chromium phosphate.

The catalyst of the present invention provides a high yield of reaction without the use of a carrier. It may be used with a suitable amount of carrier, however, for the purpose of adding to the strength of the catalyst and enhancing the catalyst's thermal resistivity.

As for the carrier, a substance such as silicon carbide powder, aluminum powder, α-alumina or celite, which is chemically inert to methacrolein and methacrylic acid, may be used.

In carrying out the process of this invention, it is desirable to have the reaction temperature fall within the range of 200° to 400° C, and preferably within 230° to 370° C.

The amount of raw gas to be supplied is desired to be such as to give a space velocity within the range of 100 to 3000 liters of gas/liter of catalyst per hour, and preferably from 250 to 1500 liters of gas/liter of catalyst per hour. Actually, optimum reaction conditions are selected in accordance with the percentage of the components of the catalyst, reaction temperature, proportion of the catalyst to its carrier, etc.

The reaction can be carried out under increased or decreased pressure. Generally, pressure in the neighborhood of atmospheric pressure is suitable.

The catalyst of this invention can be used in the form of a fixed bed, a fluid bed or a moving bed. The present invention will be described more specifically herein below with reference to preferred embodiments thereof.

The conversion of methacrolein, the selectivity of methacrylic acid, the yield of methacrylic acid and the space velocity have been calculated in accordance with the following respective definitions.

Conversion of methacrolein (%) =

$$\frac{\text{Number of mols of converted methacrolein}}{\text{Number of mols of supplied methacrolein}} \times 100$$

Selectivity of methacrylic acid (%) =

$$\frac{\text{Number of mols of formed methacrylic acid}}{\text{Number of mols of converted methacrolein}} \times 100$$

Yield of methacrylic acid (%) =

$$\frac{\text{Number of mols of formed methacrylic acid}}{\text{Number of mols of supplied methacrolein}} \times 100$$

Space velocity (SV) =

$$\frac{\text{Flow volume of raw gas (in NTP) (liters of gas/hr)}}{\text{Volume of packed catalyst (liters of catalyst)}}$$

The yield of acetic acid, carbon dioxide and carbon monoxide by-products in the reaction, have been calculated in accordance with the following respective definitions.

Yield of acetic acid (%) =

$$\frac{\text{Number of mols of formed acetic acid}}{\text{Number of mols of supplied methacrolein}} \times \frac{1}{2} \times 100$$

Yield of carbon dioxide (%) =

$$\frac{\text{Number of mols of formed carbon dioxide}}{\text{Number of mols of supplied methacrolein}} \times \frac{1}{4} \times 100$$

Yield of carbon monoxide (%) =

$$\frac{\text{Number of mols of formed carbon monoxide}}{\text{Number of mols of supplied methacrolein}} \times \frac{1}{4} \times 100$$

EXAMPLE 1

In a ball mill, 84.2 g of phosphomolybdic acid, 10.5 g of copper chromate, 19.4 g of atimony trioxide, 7.5 g of ammonium phosphate, 22.5 g of aqueous 28% ammonia water and 40 ml of deionized water were placed and blended for 24 hours. The cakey substance consequently obtained was dried for 3 hours in a drier at 120° – 130° C, thereafter crushed to a particle size of 8 to 20 mesh, packed into a quartz tube with a 25 mm inside diameter and a length of 50 cm and subjected to a calcination treatment at 400° C for 7 hours under the supply of air at a rate of 4 liters/hour. The catalyst thus prepared had the following composition:

$$Mo_{12}P_{2.7}Sb_{3.7}Cu_{2.4}Cr_{0.79}O_{54}(NH_4)_{2.7}$$

A 20-ml portion of this catalyst was then packed into a stainless steel reactor with a 20 mm inside diameter and raw feed gas, consisting of methacrolein, oxygen, steam and nitrogen at a molar ratio of 1 : 4.1 : 10.9 : 15.5, was introduced therein at a space velocity of 1000 hr$^{-1}$ and a temperature of 270° C to cause an oxidation reaction. The results of this reaction were 87.5% methacrolein conversion, 81.4% methacrylic acid selectivity, 71.2% methacrylic acid yield, 4.5% acetic acid yield, 5.4% carbon dioxide yield and 4.5% carbon monoxide yield.

EXAMPLE 2

A solution of 56.1 g of phosphomolybdic acid in 150 ml of deionized water was mixed with 2.4 g of copper chromate and 12.5 g of antimony trioxide. The mixture was stirred at 50° C for two hours, then mixed further with 5.0 g of ammonium phosphate and 15 ml of aqueous 28% ammonia water. The resultant suspended solution was then evaporated to dryness under agitation. The cakey substance formed was consequently subjected to the same treatment noted in Example 1. The catalyst thus prepared has the following composition.

$$Mo_{12}P_{2.7}Sb_{3.6}Cu_{0.81}Cr_{0.27}O_{49}(NH_4)_{2.7}$$

A 20-ml portion of this catalyst was then packed into a reaction tube and raw feed gas, having the same composition as that in Example 1, was supplied at a space velocity of 1000 hr$^{-1}$ and a temperature of 310° C to cause an oxidation reaction.

The results of the reaction were 87.0% methacrolein conversion, 77.8% methacrylic acid selectivity and 67.7% methacrylic acid yield.

EXAMPLE 3

A reaction tube was packed with 40 ml of the catalyst, as prepared in Example 2, and raw gas, having the same composition as that of Example 1, was supplied at a space velocity of 500 hr$^{-1}$ and a temperature of 280° C to cause an oxidation reaction. The results of the reaction were 92.5% methacrolein conversion, 79.8% methacrylic acid selectivity, 73.8% methacrylic acid yield, 5.7% acetic acid yield, 6.5% carbon dioxide yield and 5.9% carbon monoxide yield.

EXAMPLE 4 to 12:

Nine catalysts were prepared and used for the oxidation of methacrolein by following the procedure noted in Example 1, except for the changes in the catalyst composition and reaction temperature as indicated in Table 1. The results are shown in Table 1.

TABLE 1

| Example No. | Catalyst composition | Reaction temperature (° C) | Conversion of methacrolein (%) | Selectivity of methacrylic acid(%) | Yield of methacrylic acid(%) |
|---|---|---|---|---|---|
| 4  | $Mo_{12}P_{2.7}Sb_{3.7}Cu_{0.47}Cr_{0.96}O_{50}(NH_4)_{2.7}$ | 320 | 86.5 | 71.6 | 61.9 |
| 5  | $Mo_{12}P_{2.7}Sb_{3.6}Cu_{4.1}Cr_{1.4}O_{55}(NH_4)_{2.6}$ | 270 | 92.0 | 75.5 | 69.5 |
| 6  | $Mo_{12}P_{1.7}Sb_{3.7}Cu_{2.4}Cr_{0.79}O_{49}(NH_4)_{2.5}$ | 280 | 89.0 | 70.5 | 62.7 |
| 7  | $Mo_{12}P_{3.5}Sb_{3.7}Cu_{2.4}Cr_{0.79}O_{55}(NH_4)_{2.7}$ | 305 | 86.5 | 71.5 | 61.8 |
| 8  | $Mo_{12}P_{2.7}Sb_{5.8}Cu_{2.4}Cr_{0.79}O_{56}(NH_4)_{2.6}$ | 295 | 88.4 | 75.4 | 66.7 |
| 9  | $Mo_{12}P_{2.7}Sb_{3.7}Cu_{2.4}Cr_{3.6}O_{58}(NH_4)_{2.9}$ | 295 | 89.5 | 78.5 | 70.3 |
| 10 | $Mo_{12}P_{2.7}Sb_{3.7}Cu_{2.4}Cr_{5.4}O_{58}(NH_4)_{2.8}$ | 305 | 87.0 | 70.5 | 61.3 |
| 11 | $Mo_{12}P_{2.7}Sb_{0.82}Cu_{0.81}Cr_{0.27}O_{45}(NH_4)_{2.7}$ | 300 | 92.0 | 64.1 | 59.0 |
| 12 | $Mo_{12}P_{2.7}Sb_{3.7}Cu_{2.4}Cr_{0.79}O_{54}(NH_4)_{1.5}$ | 285 | 84.9 | 72.1 | 61.2 |

The space velocity at which the raw feed gas was supplied was 1000 hr$^{-1}$ in Examples, 4, 6, 8, 11 and 12, 700 hr$^{-1}$ for Examples 7, 9 and 10 and 1400 hr$^{-1}$ for Example 5, respectively.

EXAMPLE 13

A catalyst was prepared by following the procedure noted in Example 1, except that 7.5 g of ortho-phosphoric acid was used in place of 7.5 g of ammonium phosphate and the addition of aqueous 28% ammonia water was omitted. The catalyst thus obtained had the following composition:

$Mo_{12}P_{2.7}Sb_{3.7}Cu_{2.4}Cr_{0.79}O_{54}$

Raw feed gas, having the same composition as that of Example 1, was supplied at a space velocity of 700 hr$^{-1}$ and a temperature of 335° C to cause an oxidation reaction similarly to Example 1. The results of the test were 90.5% methacrolein conversion, 64.1% methacrylic acid selectivity and 58.0% methacryacid yield.

EXAMPLE 14

A solution was obtained by dissolving 200 g of ammonium molybdate in 400 ml of distilled water at 70° C. This solution was mixed with 20 ml of aqueous 28% ammonia water and further with 15.6 g of copper pyrophosphate. Subsequently, 48.4 g of antimony trioxide was slowly added thereto. Then 30 ml of an aqueous solution containing 19.2 g of ammonium phosphate was added thereto. The suspended solution consequently formed was evaporated to dryness while under agitation. The cakey substance thus obtained was dried for about three hours in a drier at 120° – 150° C, crushed to a particle size of 8 – 20 mesh and packed in a quartz tube with a 25 mm inside diameter and a length of 50 cm and then subjected to calcination treatment at 405° C for seven hours under a supply of air at the rate of 4 liters per hour. The catalyst thus prepared had the following composition.

$Mo_{12}P_{2.6}Sb_{3.5}Cu_{0.63}O_{49}(NH_4)_{2.6}$

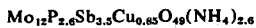

Twenty mls of this catalyst was packed in a stainless steel reactiion tube with a 20 mm inside diameter and raw feed gas consisting of methacrolein, oxygen, steam and nitrogen at a molar ratio of 1 : 1.8 : 18 : 20 was supplied thereto at a contact time of 4 seconds (SV = 900 hr$^{-1}$) and a temperature of 285° C to cause an oxidation reaction. The results of this reaction were 93.8% methacrolein conversion, 73.8% methacrylic acid selectivity and 69.2% methacrylic acid yield.

EXAMPLE 15

The catalyst of Example 14 was calcined at 390° C while under the supply of air at a rate of 4 liters per hour and thereafter subjected to a preliminary treatment at 300° C under a current of methacrolein containing therein isobutylene. The catalyst was again calcined for 7 hours at 390° C and subjected to the reaction. The oxidation reaction was carried out under the same conditions as noted in Example 14, except for the reaction temperature which was 297° C. The results were 93.6% methacrolein conversion, 74.8% methacrylic acid selectivity and 70.0% methacrylic acid yield.

EXAMPLE 16

At room temperature, 56.1 g of phosphomolybdic acid was dissolved in 150 ml of distilled water. The solution was mixed with 20 ml of aqueous 28% ammonia water followed by 7.8 g of copper pyrophosphate. Then, 12.1 g of antimony trioxide was slowly added thereto. The suspended solution, consequently formed, was evaporated to dryness while under thorough agitation. The cakey substance thus obtained was dried for about 3 hours in a drier between 120° – 150° C, crushed to a particle size of 8 – 20 mesh, packed in a quartz tube with a 25 mm inside diameter and a length of 50 cm and then subjected to calcination treatment for 7 hours at 390° C under supply of air at a rate of 4 liters per hour. The catalyst thus produced had the following composition.

$Mo_{12}P_{2.7}Sb_{3.5}Cu_{1.7}O_{50}(NH_4)_{2.6}$

This catalyst was subjected to a preliminary treatment at 280° C with an isobutylene-containing methacrolein, then recalcined for 7 hours at 390° C and thereafter put to use in the reaction. The oxidation reaction was carried out under the same reaction conditions as those noted in Example 14, except for the reaction temperature which was 270° C. The results of the reaction were 96.6% methacrolein conversion, 70.2% methacrylic acid selectivity and 67.8% methacrylic acid yield.

EXAMPLE 17

A catalyst having the following composition was prepared by following the procedure in Example 14.

$Mo_{12}P_{2.7}Sb_{3.5}Cu_{0.76}O_{50}(NH_4)_{2.6}$

A 40-ml portion of this catalyst was packed into a stainless steel reaction tube with a 20 mm inside diameter. Raw gas consisting of methacrolein, oxygen, steam and nitrogen at a molar ratio of 1 : 4.1 : 10.9 : 15.5 was supplied thereto at a contact time of 3.9 seconds (space velocity = 920 hr$^{-1}$) and a reaction temperature of 280° position and reaction temperature as indicated in Table 2 below.

TABLE 2

| Example No. | Catalyst composition | Reaction temperature (° C) | Conversion of methacrolein(%) | Selectivity of methacrylic acid(%) | Yield of methacrylic acid(%) |
|---|---|---|---|---|---|
| 19 | $Mo_{12}P_{1.7}Sb_{3.5}Cu_{1.7}O_{47}(NH_4)_{2.4}$ | 290 | 89.5 | 65.0 | 58.2 |
| 20 | $Mo_{12}P_{2.2}Sb_{3.5}Cu_{1.7}O_{51}(NH_4)_{2.6}$ | 295 | 85.0 | 68.8 | 58.5 |
| 21 | $Mo_{12}P_{2.2}Sb_{1.8}Cu_{1.7}O_{46}(NH_4)_{2.6}$ | 300 | 92.0 | 62.3 | 57.3 |
| 22 | $Mo_{12}P_{2.7}Sb_{3.5}Cu_{1.7}O_{49}(NH_4)_{2.5}$ | 315 | 90.0 | 74.0 | 66.6 |
| 23 | $Mo_{12}P_{2.7}Sb_{3.5}Cu_{0.7}O_{50}(NH_4)_{1.3}$ | 290 | 88.8 | 70.4 | 62.5 |

C to cause an oxidation reaction. The results of the reaction were 90.6% methacrolein conversion, 84.4% methacrylic acid selectivity and 76.5% methacrylic acid yield. The yield of acetic acid was 3.5%, that of carbon dioxide-5.3% and that of carbon monoxide-4.2% respectively.

EXAMPLE 18

A catalyst having the following composition was prepared from 56.1 g of phosphomolybdic acid, 4.4 g of copper molybdate, 12.9 g of antimony trioxide and 5.0 g of 85% orthophosphoric acid by repeating the procedure noted in Example 14 with the necessary modifications.

An oxidation reaction was carried out by using this catalyst, similarly noted in Example 14, except for the reaction temperature which was 330° C. The results of the reaction were 81.5% methacrolein conversion, 62.5% methacrylic acid selectivity and 50.9% methacrylic acid yield.

EXAMPLE 19 to 23

Five catalysts were prepared and used for the oxidation of methacrolein by following the procedure noted in Example 16, except for the changes in catalyst composition and reaction temperature as indicated in Table 2 below.

We claim:
1. A catalyst for oxidizing unsaturated aldehydes to the corresponding unsaturated carboxylic acids having the following composition:

(wherein, the subscripts $a$, $b$, $c$, $d$, $e$, and $f$ denote the numbers respectively of molybdenum, phosphorus, antimony, copper, chromium and oxygen atoms and the subscript $g$ denotes the number of ammonium groups and, where $a$ is fixed at 12, $b$ assumes a value of 1 to 4, $c$ a value of 0.1 to 7, $d$ a value of 0.1 to 5, $e$ a value of 0 to 6 and $g$ a value of 0 to 3.5 respectively and $f$ a value, from 35 to 80, which is automatically determined by the valence of the other atoms), said catalyst being prepared by mixing starting materials containing the component elements, where necessary, in conjunction with aqueous ammonia water, drying the resulting mixture and calcining the dried mass between 300°–500° C.

2. The oxidation catalyst of claim 1, wherein $a$ is 12, $b$ is 1.5 to 3.5, $c$ is 0.5 to 6, $d$ is 0.3 to 4.5, $e$ is 0.1 to 4, $f$ is 40 to 70 and $g$ is 1 to 3.5.

3. The oxidation catalyst of claim 1, wherein $a$ is 12, $b$ is 2 to 3, $c$ is 2 to 4, $d$ is 0.5 to 2.5, $e$ is 0.5 to 1.5, $f$ is 45 to 57 and $g$ is 2 to 3.

* * * * *